United States Patent [19]

Ferrando et al.

[11] Patent Number: 4,737,147
[45] Date of Patent: Apr. 12, 1988

[54] CATHETER PROVIDED WITH AN ADDITIONAL CANALIZATION

[75] Inventors: Ugo Ferrando; Giovanni Gardi; Giustino Pagliano, all of Torino, Italy

[73] Assignee: N.U.S. S.r.l., Turin, Italy

[21] Appl. No.: 885,324

[22] Filed: Jul. 14, 1986

Related U.S. Application Data

[63] Continuation-in-part of Ser. No. 741,826, Jun. 6, 1985, abandoned.

[51] Int. Cl.$^4$ ............................................. A61M 25/00
[52] U.S. Cl. .......................................... 604/96; 604/43
[58] Field of Search ...................... 604/43, 95, 96–103, 604/265; 128/DIG. 21; 1/7

[56] References Cited

U.S. PATENT DOCUMENTS

| | | | |
|---|---|---|---|
| 1,045,326 | 11/1912 | Ruflin | 604/43 |
| 2,981,254 | 4/1961 | Vanderbilt | 604/96 |
| 3,169,527 | 2/1965 | Sheridan | 604/265 |
| 3,604,426 | 9/1971 | Erickson | 604/265 |
| 3,630,206 | 12/1971 | Gingold . | |
| 3,811,448 | 5/1974 | Morton | 604/102 |
| 3,962,519 | 6/1976 | Rüsch et al. | 128/DIG. 21 |
| 3,983,879 | 10/1976 | Todd | 604/96 |
| 4,083,369 | 4/1978 | Sinnreich | 604/96 |
| 4,257,421 | 3/1981 | Beal | 604/265 |
| 4,501,580 | 2/1985 | Glassman | 604/43 |
| 4,579,554 | 4/1986 | Glassman | 604/102 |

FOREIGN PATENT DOCUMENTS

| | | | |
|---|---|---|---|
| 2240026 | 3/1975 | France | 604/43 |
| 193885 | 1/1965 | Sweden | 604/95 |

*Primary Examiner*—Dalton L. Truluck
*Attorney, Agent, or Firm*—Browdy and Neimark

[57] ABSTRACT

An elastomeric medical catheter includes an end portion from which liquid is removed to the catheter interior and grooves on the outer periphery of a portion proximal to the distal end portion. These grooves permit the expulsion of liquid which might otherwise be trapped in the interstice between the catheter wall and the walls of the passage defining the entrance of the orifice into which the catheter is inserted. By permitting the naturally occurring pressure difference between the orifice and the ambient to expel liquid which is in the interstice, liquid stasis is avoided and potentially dangerous bacteria are flushed from the interstice.

7 Claims, 2 Drawing Sheets

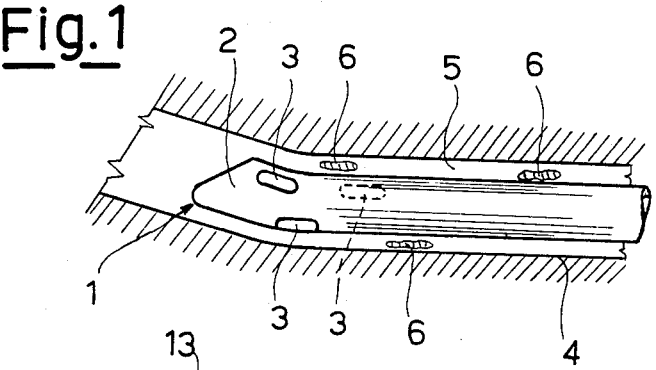
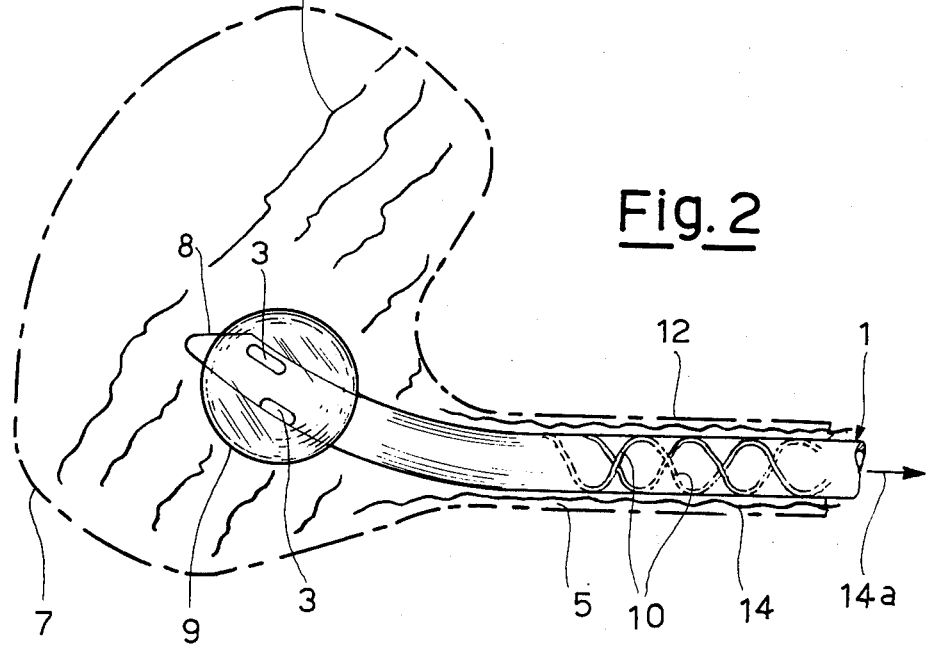

CATHETER PROVIDED WITH AN ADDITIONAL CANALIZATION

This application is a continuation-in-part of application Ser. No. 741,826, filed June 6, 1985, now abandoned.

BACKGROUND OF THE INVENTION

This invention relates to a catheter for medical application, and more particularly to a catheter designed for a specific function.

It is known that a catheter is generally intended to be used for the drainage of physiological and medicinal liquids from human body organs in various surgical fields, such as, for example, urology, in connection with renal or vesical fluxes, gastroenterology, with expulsion of pus mixed with blood, and neurosurgery, with expulsion of cerebral liquids interposed between the convolution walls and the parietal wall. The presence of these liquids could result in preoperative and postoperative complications.

Conventionally, drainage is performed by a catheter made of a silicone material or the like having a certain degree of elasticity and the shape of a conduit. Introduction of such a catheter into the orifice of the human body, however, requires the application of a lubricant film, usually of petroleum jelly, onto the catheter outer surface to facilitate the introduction of the catheter to avoid painfully traumatizing the patient by friction during insertion.

However, the presence of the lubricant film causes a serious complication. The interstice formed between the inner surface of the orifice and the outer surface of the conduit is quite small and stasis of the fluids being drained can occur therein. Also, a scarcity of oxygen arises within this small interstice. Both liquid stasis and scarcity of oxygen can promote the growth of bacteria, resulting in dangerous infections.

SUMMARY OF THE INVENTION

It is an object of the invention to eliminate the aforementioned disadvantages together with their harmful effects.

It is another object of the present invention to provide a catheter of simple and easy construction, having a long operative life and reduced manufacturing costs.

To obtain these objects and advantages together with others which will appear in the course of the following detailed description, a catheter made of an elastomeric silicone material and the like is provided. The outer peripheral surface of the catheter is adapted for sliding into a passage leading into a body orifice. The distal end region of the catheter is designed to remove fluid from the orifice of the human organ. The outer peripheral surface of a region distal to the proximal end region includes a canalization adapted to ensure the expulsion of external physiological liquid or the like, even in case of a reduced delivery thereof, in a direction coaxial to the inner drainage space of the catheter. This expulsion permits the axial escape of bacteria. The expulsion of external fluid is driven by the ever present difference in pressure between said orifice and the surrounding outer ambient.

BRIEF DESCRIPTION OF THE DRAWINGS

A practical and preferred solution given by way of a non-limiting example will now be described with reference to the annexed drawings, in which:

FIG. 1 is a diagrammatic front view of a known conventional catheter; and

FIG. 2 is a side view showing the catheter of the present invention.

DETAILED DESCRIPTION OF THE PREFERRED EMBODIMENTS

Figure 3:
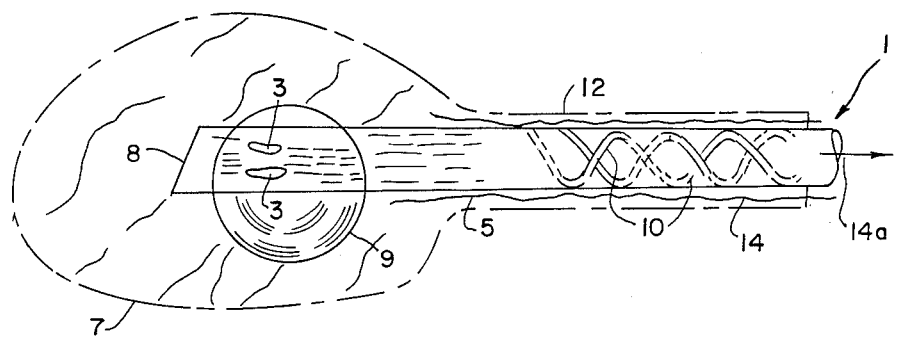
FIG. 3 is a top view showing the catheter of the present invention.

Reference is now made to the above Figures and the description of the medical device is herein limited only to those parts relevant to an understanding of the present invention. FIG. 1 indicates generally a conventional catheter made, as is the catheter of the present invention, of a silicone material or the like and therefore having a comfortable degree of softness.

For the drainage of the various physiological liquids from the human organism through the catheter end region the end region is provided with moderately three dimensioned through holes 3.

The catheter is passed into the orifice 4 after having been lubricated on its outer surface in order to facilitate its sliding without traumatizing the patient.

According to the known prior art shown in FIG. 1, there appears the moderate annular dimensioning of the interstice 5 defined by the respective surfaces, i.e. the inner surface of the orifice and the outer surface of the catheter 1.

In interstice 5, because of the dimensioning, and above all because of the presence of the outer lubricating film, a stasis of liquid may occur. This stasis encourages the growth of bacterial colonies 6, increasing the risk of infection.

According to the present invention, this risk is eliminated by a simple but efficient catheter design.

As diagrammatically shown in FIG. 2, the catheter 1 is inserted, for example, into an orifice including the patient's vesica 7 and the urethral passage leading thereto. The vesica contains a physiological liquid 13 which is removed through distal end 8, including holes 3. Distal end 8 is stabilized by a known synthetic balloon 9, inflatable by pneumatic action by means of a valve and positioned on the opposite end (not shown) of the catheter. Balloon 9 is non-coaxial with catheter 1, i.e., balloon 9 is balanced to one side (any side) thereof (FIG. 3). Thus, the balloon does not block the inlet of urethra 12 or obstruct the flow of urine along channels 10. Grooves 10 extend along the outer periphery of the proximal end region proximal to distal end 8.

These grooves are formed, for example, by two sets of intersecting grooves having a continuous sinusoidal profile along the outer peripheral surface of the catheter. Grooves or canalizations 10 ensure the expulsion of physiological liquid 13, from vesica 7, in interstice 5.

This expulsion results from the pressure head between the interior of the vesica 7 and the outer ambient (the pressure in vesica 7 is higher than ambient). The fluid flow through interstice 5 removes bacterial colonies 6, which may be suitably collected.

The main inner drainage, as indicated in FIG. 2 by the arrow 14a, is also collected in an appropriate pocket.

In addition to this antibacterial drainage, the canalizations 10 ensure, by their presence, the conveyance of the necessary lubricating product, thereby facilitating the introduction of the catheter into the orifice of the involved organ.

Grooves 10, may be easily formed by a plurality of intersecting grooves having similar profiles. Grooves 10 may be produced, for example, by hot-drawing or pressing. Grooves 10 may also be produced on already existing medicinal tubes.

Obviously, the practical embodiments of the catheter may vary within wide limits, without departing from the invention, as protected by the annexed claims.

We claim:

1. A medical catheter made of elastomeric material and adapted to extend within a vesica of a human body, said catheter comprising:

slidably inserted adapted to reside within the vesica and having means for removing fluid from said vesica through the interior of said catheter;

an outer peripheral surface, adapted slidably inserted be slid within a passage leading into said vesica;

an inflatable balloon attached to said end region and being mounted such that it is adapted to inflate so that said balloon, when inflated condition, is non-coaxial with said catheter;

a proximal end region proximal to said distal end region, wherein said outer peripheral surface defines a plurality of grooves longitudinally extending for a majority of the length of said passage when said end region is residing within said vesica, said plurality of longitudinally extending grooves defining means for coaxial passage of liquid and bacteria from an area of higher pressure due to said vesica to an area of lower pressure due to ambient pressure whereby said passage results from the pressure differential between said vesica and ambient pressure, said plurality of longitudinally extending grooves not being in communication with any other passages provided in said catheter, said outer peripheral surface being imperforate between the balloon and the ends of said longitudinally extending grooves closest to said balloon.

2. The catheter of claim 1 wherein said outer peripheral surface is coated with a lubricant.

3. The catheter of claim 1 wherein said grooves form two essentially identically shaped, intersecting, sinusoidal patterns.

4. The catheter of claim 1 wherein said elastomeric material is silicone.

5. A medical catheter of a soft, elastomeric material, adapted to extend through a passageway and into a vesica of a human body, said catheter comprising:

an elongated hollow catheter body portion having an outer peripheral surface adapted to be slidably inserted within the passageway leading into the vesica;

a distal end region adapted to reside within the vesica, said distal end region having means for removing fluid from said vesica through the interior of said catheter;

means to retain said distal end region within the vesica without blocking the passageway, said means including an inflatable balloon attached to said distal end region and being mounted such that it is adapted to inflate so that said balloon, when inflated condition, is non-coaxial with said catheter so as not to block the passageway; and a proximal end region, proximal to said distal end region, of said catheter body where said outer peripheral surface defines a plurality of grooves longitudinally extending for a majority of the length of said passage when said distal end region is residing within said vesica, said plurality of longitudinally extending grooves defining means for coaxial passage of liquid and bacteria from a zone of higher to a zone of lower pressure whereby said coaxial passage results from the pressure differential between a higher pressure in said vesica and ambient pressure, said plurality of longitudinally extending grooves not being in communication with any other passages provided in said catheter and said outer peripheral surface being imperforate between said balloon and the ends of said longitudinally extending grooves closest to said balloons.

6. A method of draining physiological liquid from a vesica of a human being at a pressure higher than the outer ambient, said method comprising the steps of:

inserting a catheter having a distal end region, said distal end region including means for removing fluid from said vesica through the interior of said catheter, an inflatable balloon, in uninflated condition, attached to said distal end region, the balloon being mounted such that, when inflated, it is non-coaxial with said catheter, and a proximal end region proximal to said distal end region, at where said outer peripheral surface defines a plurality of longitudinally extending grooves which are not in communication with any other passages provided in the catheter, into said vesica through an orifice of a body passage leading into said vesica so that said uninflated balloon is fully contained within the vesica, the longitudinally extending grooves longitudinally extend in the direction of the balloon, from near the orifice, for a majority of the length of the body passage, said outer peripheral surface being imperforate between said balloon and the junction of said body passage with said vesica and a proximal end of the catheter extends outside the orifice; and inflating said balloon whereby said means for removing fluid drains fluid from said vesica.

7. The method of claim 6 wherein said vesica is the urinary bladder and said passage is the urethral canal extending from said bladder.

* * * * *